United States Patent [19]

Chen

[11] Patent Number: 4,997,439
[45] Date of Patent: Mar. 5, 1991

[54] SURGICAL CLOSURE OR ANASTOMOTIC DEVICE

[76] Inventor: Fusen H. Chen, 12 Vernon La., Thompson, Conn. 06277

[21] Appl. No.: 472,209

[22] Filed: Jan. 26, 1990

Related U.S. Application Data

[63] Continuation-in-part of Ser. No. 303,326, Jan. 26, 1989, Pat. No. 4,676,245.

[51] Int. Cl.$^5$ ............................................... A61B 17/00
[52] U.S. Cl. ................................... 606/216; 606/213
[58] Field of Search ............................ 606/213–216, 606/220, 221

[56] References Cited

U.S. PATENT DOCUMENTS

| | | | |
|---|---|---|---|
| 3,825,010 | 7/1976 | McDonald | 606/216 |
| 4,430,998 | 2/1984 | Harvey et al. | 606/216 |
| 4,526,173 | 7/1985 | Sheehan | 606/216 |
| 4,637,380 | 1/1987 | Orejola | 606/216 |
| 4,676,245 | 6/1987 | Fukuda | 606/216 |
| 4,924,866 | 5/1990 | Yoon | 606/216 |

*Primary Examiner*—Randall L. Green
*Assistant Examiner*—Gary Jackson
*Attorney, Agent, or Firm*—Morris Kaplan

[57] ABSTRACT

Elongated, flexible strip, for linear or tubular surgical joinder has pluralities of primary retaining pins that extend in opposed directions and are substantially parallel to the strip face. The pins are adapted to pierce a respective tissue, extend therealong, and then extend into the opposed tissue of a surgical opening. Short retaining pins extending normal to the strip are adapted to inhibit withdrawal of the primary retaining pins. Apertures at one end of the strip operatively associate with end ones of the short pins to configure the strip for anastomosis.

4 Claims, 7 Drawing Sheets

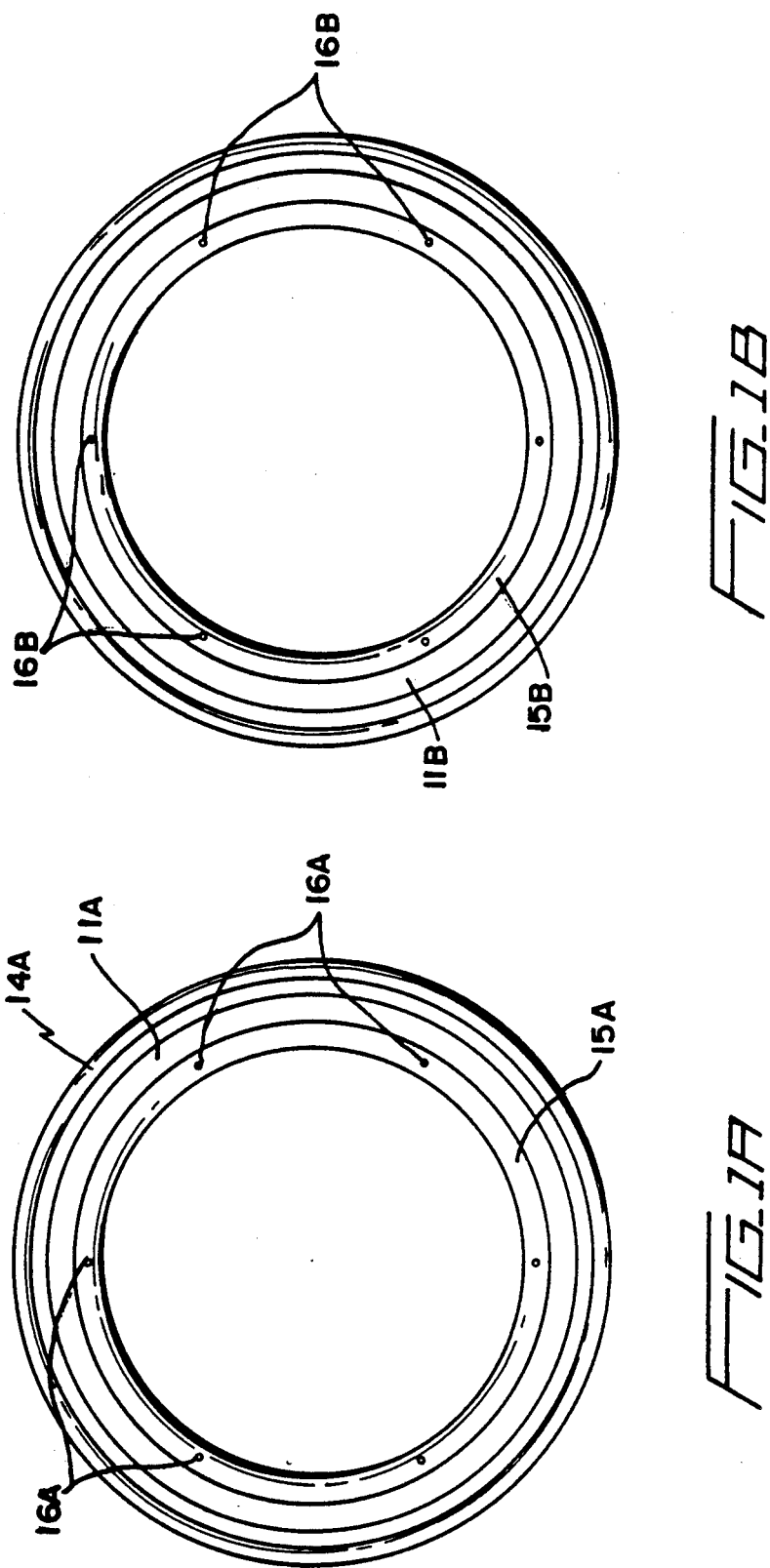

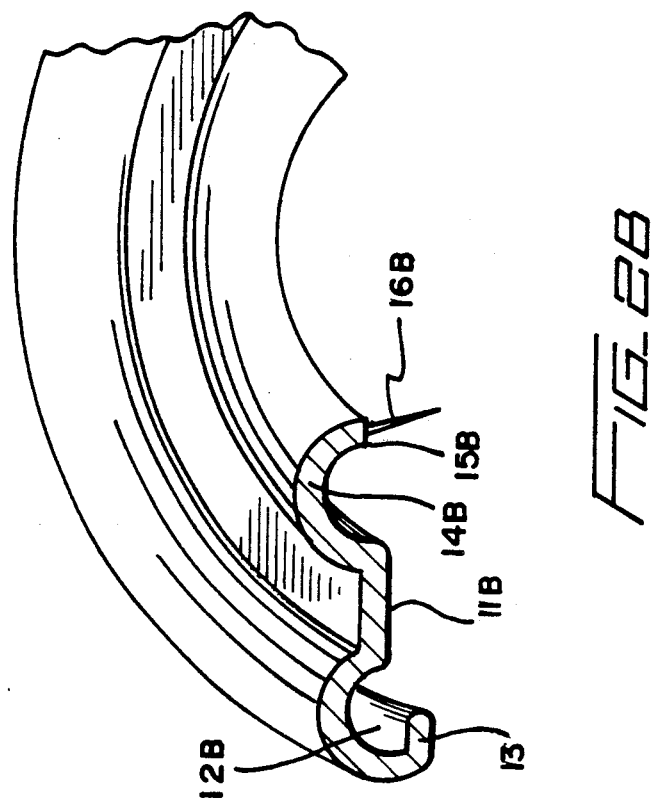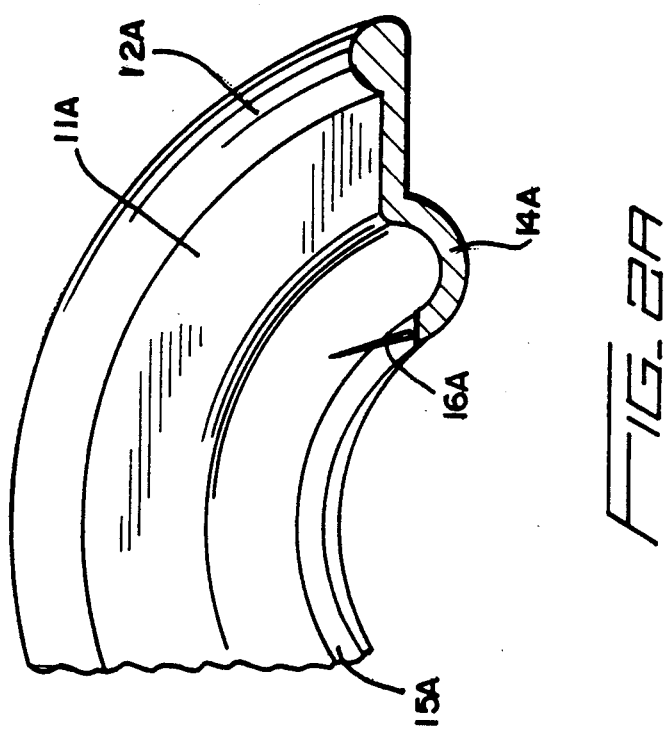

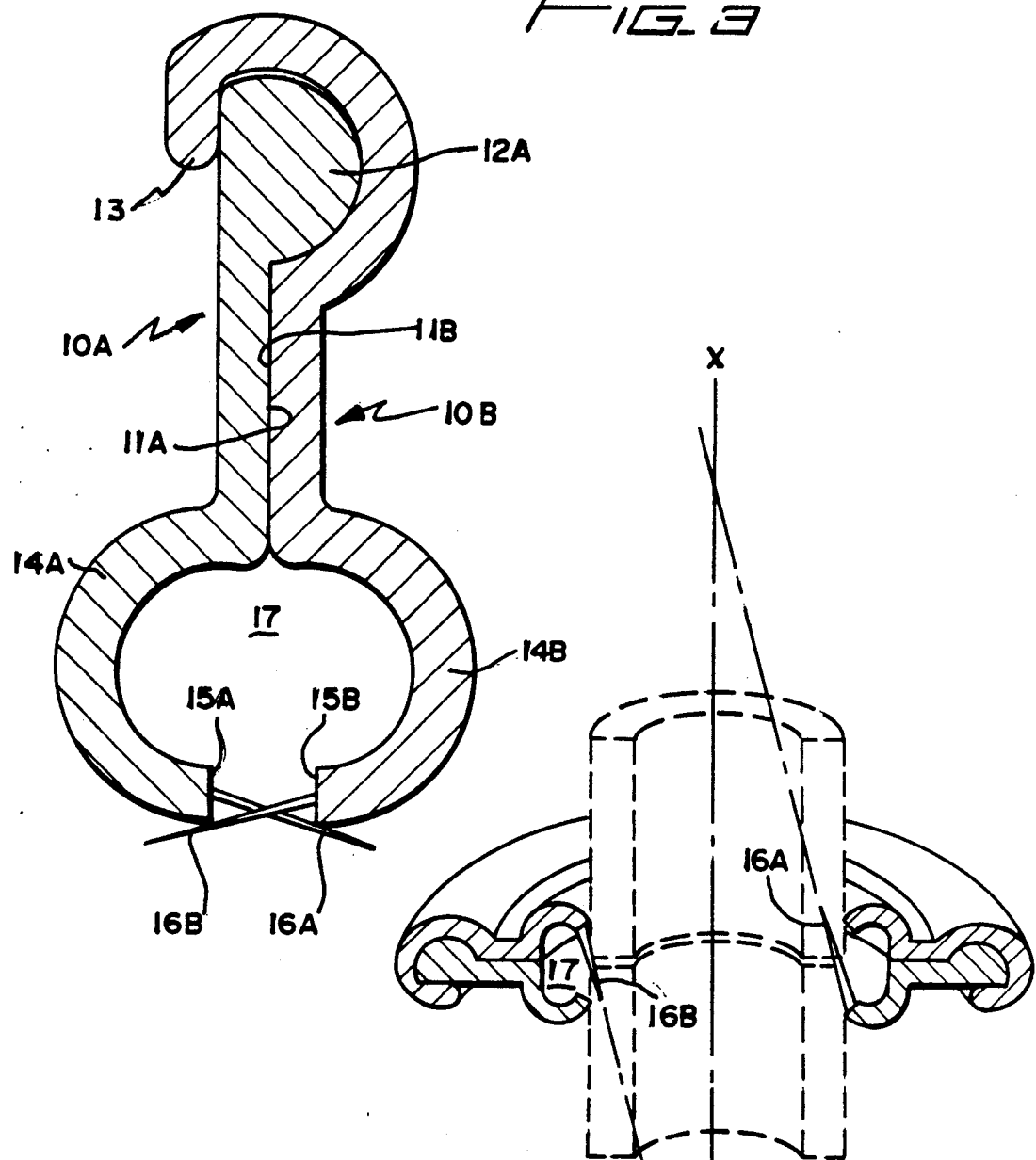

SURGICAL CLOSURE OR ANASTOMOTIC DEVICE

CROSS-REFERENCE TO RELATED APPLICATION

This application is a continuation-in-part of application Ser. No. 07/303,326, filed Jan. 26, 1989 now U.S. Pat. No. 4,676,245, issued June 5, 1990.

TECHNICAL FIELD

The present invention relates to the surgical joining of tubular structures by use of improved anastomotic devices and to adaptations thereof for surgical closure of elongate openings.

BACKGROUND OF THE INVENTION

The use of anastomotic devices is well known in the art. See, for instance, U.S. Pat. Nos. 2,453,056 (Zack); 2,638,901 (Sugarbaker); 3,155,095 (Brown); 3,254,650 (Collito); 4,233,981 (Schonmacher); 4,294,255 (Jeroe); 4,523,592 (Daniel); 4,624,255 (Shenck et al.); 4,657,091 (Walsh. et al.); 4,693,249 (Shenck et al.); 4,705,039 (Sakaguchi et al.); 4,728,328 (Hughes); and 4,747,407 (Heng et al.).

These patents are discussed in part in the above-identified parent application, the disclosure of which parent is, by reference, incorporated herein.

The known prior art devices of the type are not fully satisfactory. Some of the problems confronted are:

the device requires a pronounced eversion of the tubular structure being anastomosed;

a severe clamping pressure may be exerted which may be causative of necrosis or at least result in diminished blood flow and prolonged healing;

the device is awkward to use in contradistinction to efficient surgical procedure;

the device is relatively sophisticated with respect to manufacture and use; and the device does not allow for the inflammation and growth of tissue of the lumen.

SUMMARY OF THE INVENTION

The present invention is directed to an improved surgical device that: is mechanically simple and inexpensive to manufacture; it is easy to use to thus facilitate efficient surgical procedure; and does not require eversion and sandwiching of the structure anastomosed or excessive clamping pressure thereon or on structures of elongate openings being closed.

In a preferred embodiment of the improved device, a pair of separate ring members have operatively associated, releasable locking elements at their distal peripheries. Each said member has a series of retaining pins adapted to impale a respective first lumen, extend generally in the direction of the luminal axis, and impale a second lumen to thus effect anastomosis of the structures with their intima apposed.

Other species of improved joinder and closure devices are disclosed.

For a more fully developed presentation of the invention, and preferred embodiments thereof, reference is made to the following descriptive matter, attached drawings, and claims.

BRIEF DESCRIPTION OF THE DRAWINGS

FIGS. 1A and 1B are plan views of a preferred embodiment of an improved anastomotic device and show the inner faces to be operatively associated.

FIGS. 2A and 2B are partial perspective views corresponding to FIGS. 1A and 1B, respectively.

FIG. 3 is a radial cross-section of the preferred embodiment in operative association.

FIG. 4 shows a diametric cross-section of the preferred embodiment in association with anastomosed structures shown in broken line.

DETAILED DESCRIPTION OF THE INVENTION

Figure 5A:
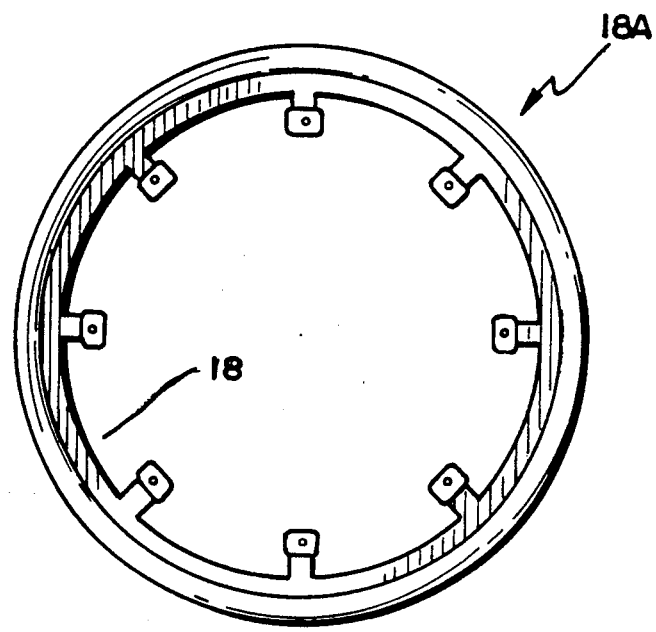
FIGS. 5A and 5B illustrate a second embodiment of the invention.

Referring to the drawings which illustrate preferred embodiments of the invention and wherein like numerals indicate like elements of structure, there is shown in FIGS. 1A–4 an anastomotic device wherein the designations A and B relate to respective male and female members or to structural elements thereof.

Male member 10A is configured as an annulus that is elongated in the radial direction which has an inwardly facing, generally planar surface portion 11A on the outer radial extent that operatively associates and abuts with surface 11B of female member 10B; see FIG. 3. An inwardly bead element 12A is disposed at the distal end of surface 11A and, in assembly, is adapted to lock into channel 12B of annulus 10B. The channel is formed with a flexible retaining flange 13.

At the proximal periphery of each annulus is a respective inwardly facing channel-forming means 14A, 14B. The free ends of said channel-forming means are shown in the assembly of FIG. 3 as spaced apart end faces 15A, 15B, each face lying outwardly of the plane extended of its respective associated planar surface 11A, 11B. A plurality of retaining pins 16A, 16B are spacedly disposed around the periphery of, and extend inwardly from, each said end face and spacedly alternate with the pins of the opposed series.

As shown in FIG. 4, and easily deducible from the radial section of FIG. 3, the pin lines extended form relatively small acute angles with the luminal axis x—x in order to maximize the length of organ impalement and to optimally effect pin extension into the opposed organ wall.

Note from FIG. 4 that the assembled device forms a composite channel 17 that bounds the area of organ joinder, that the outer edges of the end faces 15A, 15B abut the organ walls, and that the abutting faces 11A, 11B lend stability to the assembled device and to the spaced relationships thereof.

Thus, with respect to the lumen-forming members, which are illustrated by broken lines, the outflow of blood is inhibited, and the void 17 accommodates any swelling occurring at said area.

Obviously, the annular device will dimensionally vary in accordance with that of the tubular structure treated, and said end faces and pins may be variously configured to effect the aforesaid impalement and organ contact, and the number of and spacing between pins is a matter of mechanical choice and design.

In use of the improved anastomotic device of FIG. 1A through FIG. 4, a tubular section is inserted through the rear center, or backside, of a first annular member to a predetermined depth and then retracted to effect impalement. A second tubular part is likewise manipulated with respect to the second member. The members are then assembled, as illustrated in FIG. 4, whereupon each pin enters the opposed tubular part to further maintain retention and patency of the lumen.

Figure 5B:
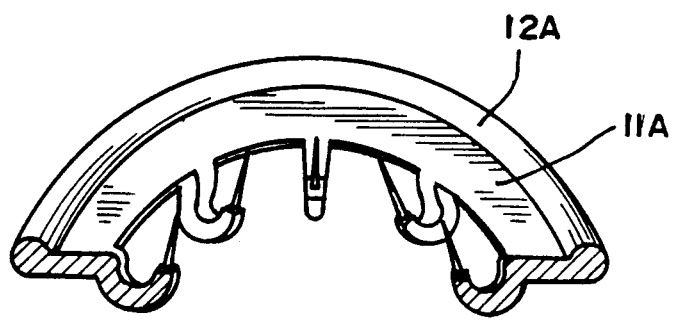

Only a male member 18A is shown in the species of invention illustrated in FIGS. 5A, 5B. This embodiment of the invention is identical to that of FIGS. 1-4, except that the male and female annuli are each slotted, as at 18, between radial sections upon which the retaining pins are mounted; the slots extending from the inner diameters. The depth and width of said slots require only that the radial sections have sufficient rigidity for the tubular retention purpose.

Figure 6:
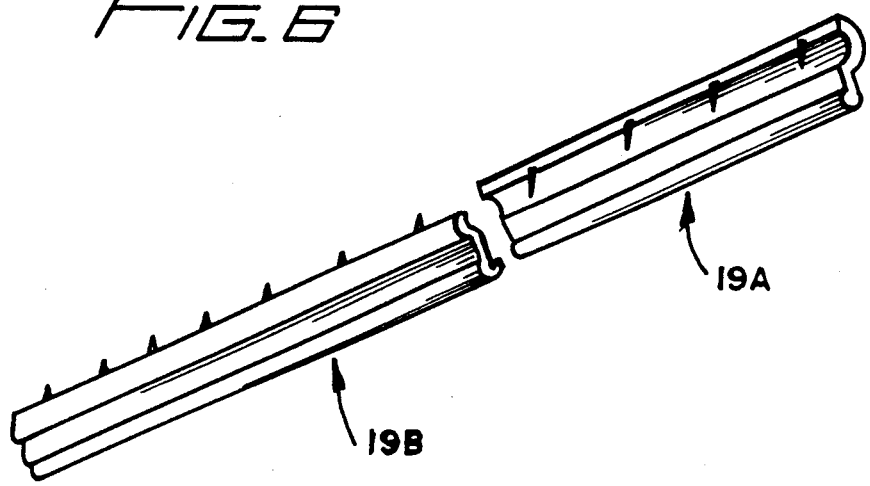
FIG. 6 illustrates a third embodiment of the invention.

The species of invention illustrated in FIG. 6 is identical to that of FIGS. 1A-4, except that the device members are not configured as annuli but are presented as strips 19A, 19B. In use, the male and female strips of predetermined lengths may be assembled with respect to luminal structure or may be utilized to close elongated openings in an anatomical wall.

Figure 7:
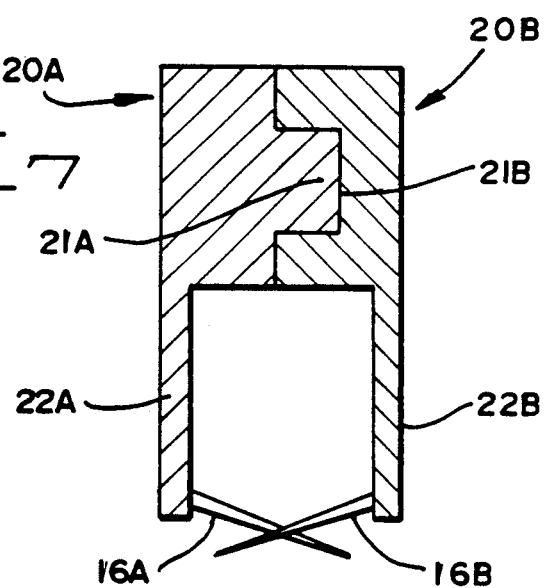
FIGS. 7 and 8 illustrate a fourth embodiment of the invention.
Figure 8:
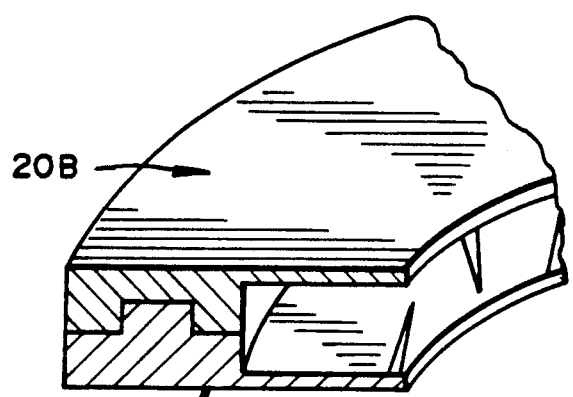

The radial section of FIG. 7 and partial perspective of FIG. 8 illustrate a fourth species of invention that is very similar to that of FIGS. 1A-4, is used in like manner, but is of a more severe design. Thus, male and female annuli 20A and 20B, respectively, are retained in assembly through a frictional fit between a simple annular slot 21B into which is keyed tenon 21A. Element 21A may be continuous. The inwardly extending annular walls of said annuli are simple planar elements 22A, 22B. From the inner peripheries of said planar elements extend pluralities of retaining pins 16A, 16B which are in functional disposition as in FIGS. 1A-4.

Figure 9A:
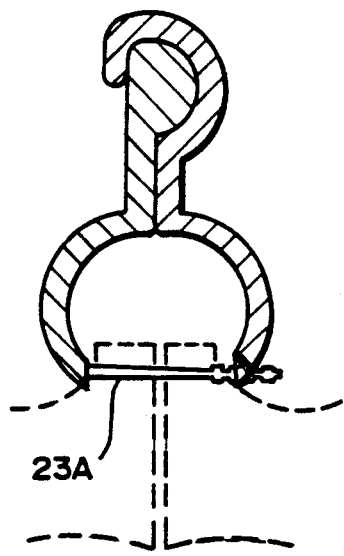
FIGS. 9A and 9B illustrate a fifth embodiment of the invention.
Figure 9B:
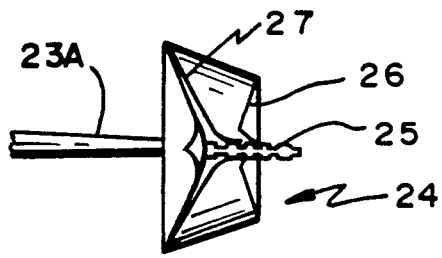

FIGS. 9A, 9B illustrate a fifth embodiment of the invention which is somewhat similarly configured as that of FIGS. 1A-4 or that of FIGS. 5A, 5B, depending on whether the aforenoted channel-forming means 14A, 14B is of continuous or slotted configuration, and materially differs only as to pin means and newly presented retaining means associated with said pins.

As in FIGS. 1A-5B, in this fifth embodiment, each annulus has a plurality of retaining pins disposed about the organ-contacting periphery thereof; the pins of each series being spaced from one another and from the pins of the opposed series with which they alternate. In this instance, however, each pin extends generally normal to the planar surface of the respective annulus, passes through each wall of the structures to be connected and then passes through pin retention means formed in the opposed annulus means.

For brevity, only one such combination of pin and retention means need be shown. Thus, in FIGS. 9A, 9B, pin 23 extends from, and generally normal to, the male member, passes through walls of structures to be connected (shown in broken line) and then through pin retention means 24. To effect such retention, each pin is peripherally notched or slotted at its distal end (as at 25 of FIG. 9B) and operatively associates with triangularly shaped, flexible panels that are formed by criss-crossing slits 26, 27, disposed in a thinned and aligned section of the opposed annulus.

Obviously, the inventive embodiment of FIGS. 7, 8 and that of FIGS. 9A, 9B may be presented in strip form, analogous to that of FIG. 6.

The sixth embodiment of the invention (10A, 10B, 10C, 10D), which is adaptable for either intraluminal joinder or for closure of an elongated opening, requires a single flexible strip 30. On one face of said strip, first and second pluralities of retaining pins 31, 32 extend from a respective intermediate transverse location, near an associated respective longitudinal strip edge 33, 34, to substantially transversely across said strip; each plurality of pins being generally aligned. The retaining pins of each plurality are spaced from one another and spaced, in the alternate, from the retaining pins of the opposed plurality.

Figure 10A:
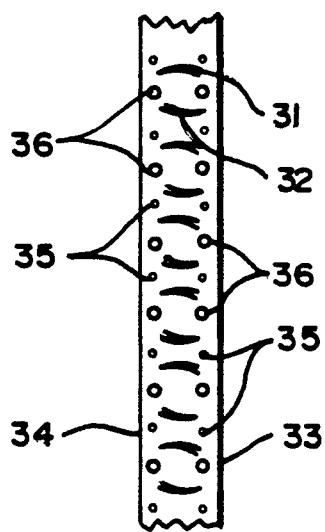
FIGS. 10A, 10B, 10C, and 10D illustrate a sixth embodiment of the invention.
Figure 10D:
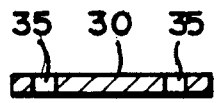

In separate longitudinal alignment, near said respective edges are first and second series of spaced and alternating apertures 35 (see the incomplete sectional view of FIG. 10D) and relatively short retaining pins 36 that extend generally normal to said strips. The short pins of the first series are in transverse alignment with the short pins of the second series, and the respective apertures are similar by aligned. Further, the transversely aligned pairs of pins and apertures are each intermediate of succeeding retaining pins 31, 32.

Figure 10B:
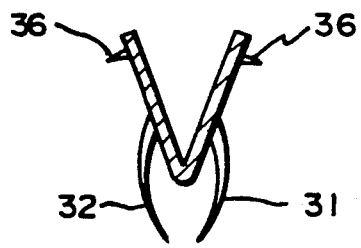
Figure 10C:
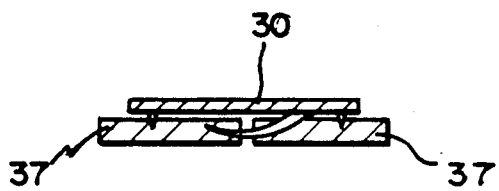

In elongate use, the strip is flexed along its longitudinal axis (note the partial flexure in the sectional view of FIG. 10B), and the anatomical parts to be joined are attached in sequence to pins 31, 32. When the strip is subsequently unflexed, the several parts assume the association as illustrated in the sectional view of FIG. 10C; wherein the short pins 36 reinforce retention of the parts joined.

When the composite strip means 30 is to be used in annular form, a requisite length of said strip is so designed that at one end is disposed a said pair of short pins and, at the other strip end, is disposed a said pair of apertures. In use as an annulus, said longitudinally and transversely aligned pairs of pins and apertures operatively associate to retain said annular form.

Figure 11A:
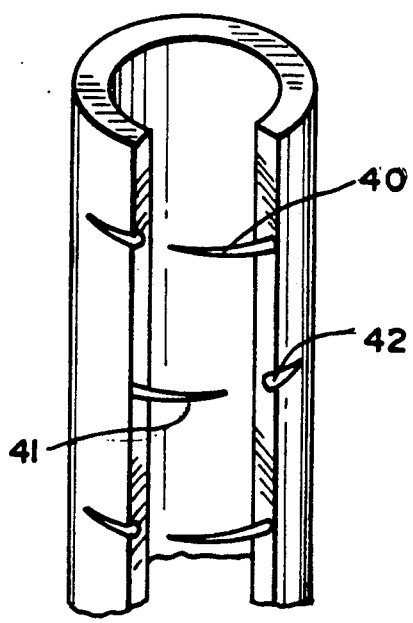
FIGS. 11A and 11B illustrate a seventh embodiment of the invention.
Figure 11B:
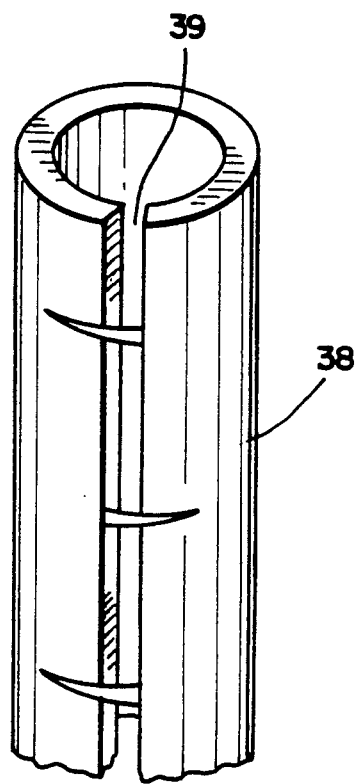

FIGS. 11A, 11B, the seventh embodiment of invention, essentially consist of a tubular member 38 that is linear if intended for closure of an elongated anatomical opening and annular if an anastomotic device. The member is relatively lightly resilient and coextensively slitted as at 39 in a line parallel to its axis or center line. Along each edge defining said slit extend a spaced plurality of retaining pins 40, 41 which extend in the path defined by the tubular structure, and each pin alternates with, and is spaced from, each respective pin that extends from the opposed edge defining such slit.

Further, each said edge is notched 42 to the extent of receiving therein a respective one of the pins extending from the opposed edge. There may be a light frictional fit between said operatively associated pins and notches.

In use, the tubular device is widened at the slit, the anatomical structures slightly flexed and attached, and the force of widening removed whereat the memory imparted in the tubular device effects closure of same or, if insufficient memory, then the tube is manipulated to effect a retained closure by means of said pins and notches.

The retaining pins may, of course, be configured to lie outside of the tubular path and to enter an anatomical wall and extend into an abutting anatomical wall, as described with respect to foregoing embodiments of the invention.

The materials of fabrication are flexible, compatible with that of the human body, and, where practical, are preferably of an absorbable such as polyglycolic or polylactic materials. Further, such latter materials of fabrication may be treated or coated in order to control the time of material dissolution, as is known in the art.

The embodiments shown and described are only illustrative he present invention and not to be construed as definitive thereof; Since once apprised of the invention, changes in structure would be readily apparent to one skilled in the art. Hence, the present invention includes all modifications of structure encompassed within the spirit and scope of the following claims.

What is claimed:

1. Surgical closure means comprising:
    a relatively thin, flexible, and manipulable ribbon comprised of a material that is compatible with the associated tissue whereat closure is to be effected;
    a first and second plurality of longitudinally aligned, spaced, generally parallel retaining pins extending in opposed directions, from and transversely across the ribbon's face that is to be operatively associated with said tissue;
    each plurality of said pins extending from a respective longitudinal side of said face to substantially the other longitudinal side of said face;
    each pin of said one plurality of pins being in a spaced and alternate relationship with respect to the opposed, said second plurality of pins; and
    each of functionally operative portions of said transversely extending pins being closely spaced from, and substantially parallel to, said face;
    whereby said surgical closure may be effected by manipulating and flexing said ribbon along the axial extent thereof and, by further manipulation, said first plurality of retaining pins is adapted to pierce said tissue on one side of the opening to be surgically closed, extend within the tissue on said one said and into the tissue on the opposed tissue side, and subsequently the opposed plurality of pins pierce the opposed tissue side, extend within opposed tissue and into the tissue on said one side.

2. Surgical closure means as in claim 1, wherein:
    a plurality of spaced, longitudinally aligned, relatively short retaining pins extends generally normal to said face of the ribbon and along each said opposite, respective longitudinal side of said face; and
    each of said short retaining pins being disposed intermediate a pair of said oppositely, transversely extending pins;
    whereby said surgical closure is enhanced by said relatively short retaining pins extending at least partially into said tissue in a direction that is generally normal to that of said transversely extending pins to thus inhibit withdrawal motion of said latter retaining pins.

3. Surgical closure means as in claim 2, wherein said relative short pins are transversely aligned.

4. Surgical closure means as in claim 3, wherein:
    a plurality of spaced apertures are disposed along each said longitudinal side of said face;
    said apertures being in longitudinal alignment with its associated plurality of said normally extending pins;
    each aperture of one said plurality being in transverse alignment with a respective aperture of the second plurality;
    each said aperture being intermediate successive ones of said normally extending pins and intermediate a pair of said oppositely transversely extending pins; and
    said apertures and normally extending pins being dimensionally operative associated;
    whereby said ribbon means, in surgical closure configuration, may be retained in annular form by associating an end pair of said normally extending pins with an end pair of said apertures and thereby effect anastomosis of members with their intima opposed.

* * * * *